United States Patent
Oyston et al.

(10) Patent No.: US 9,220,263 B2
(45) Date of Patent: Dec. 29, 2015

(54) RODENTICIDE

(75) Inventors: Petra Claire Farquhar Oyston, Salisbury (GB); Graeme Christopher Clark, Salisbury (GB)

(73) Assignee: The Secretary of State for Defense, Salisbury, Wiltshire (GB)

( * ) Notice: Subject to any disclaimer, the term of this patent is extended or adjusted under 35 U.S.C. 154(b) by 462 days.

(21) Appl. No.: 12/742,153

(22) PCT Filed: Nov. 10, 2008

(86) PCT No.: PCT/GB2008/003781
§ 371 (c)(1),
(2), (4) Date: Jul. 9, 2010

(87) PCT Pub. No.: WO2009/060225
PCT Pub. Date: May 14, 2009

(65) Prior Publication Data
US 2010/0275502 A1 Nov. 4, 2010

(30) Foreign Application Priority Data

Nov. 8, 2007 (GB) .................................. 0721937.1

(51) Int. Cl.
| | | |
|---|---|---|
| A61K 39/02 | (2006.01) | |
| A01N 37/46 | (2006.01) | |
| A01N 63/00 | (2006.01) | |
| A01N 63/02 | (2006.01) | |
| C07K 14/24 | (2006.01) | |

(52) U.S. Cl.
CPC ................ *A01N 37/46* (2013.01); *A01N 63/00* (2013.01); *A01N 63/02* (2013.01); *C07K 14/24* (2013.01)

(58) Field of Classification Search
None
See application file for complete search history.

(56) References Cited

U.S. PATENT DOCUMENTS

| 6,706,522 B1 | 3/2004 | Blattner et al. | |
|---|---|---|---|
| 7,129,271 B2 * | 10/2006 | Maupin et al. | 514/475 |
| 2006/0057178 A1 * | 3/2006 | Borchert et al. | 424/408 |

FOREIGN PATENT DOCUMENTS

| FR | 2685857 | 7/1993 |
|---|---|---|
| JP | 3145405 | 10/1989 |
| WO | WO0056282 | 9/2000 |
| WO | WO0056361 | 9/2000 |
| WO | WO0056362 | 9/2000 |
| WO | WO 03/087129 A2 * | 10/2003 |
| WO | WO03087129 | 10/2003 |
| WO | WO2006095128 | 9/2006 |

OTHER PUBLICATIONS

Van de Loo et al. (Proc. Natl. Acad. Sci U S A. Jul. 18, 1995;92(15):6743-7).*
Broun et al. (Science Nov. 13, 1998;282(5392):1315-7.).*
Song et al. DNA research vol. 11, pp. 179-197, 2004.*
YMT sequence pdf.*
Bernkop-Schnurch I (International Journal of Pharmaceutics vol. 194, pp. 1-13 2000).*
Bernkop-Schnurch II ( Crit Rev Ther Drug Carrier Syst vol. 18, 2001 Abstract only).*
Search Report in Application No. GB0721937.1 dated Mar. 6, 2008.
Cherepanov, et al., "Cloning and Detailed Mapping of Yersinia Pestis Pira plasmid FRA-YMT Region," *Molekulrna Genetlka Mikrobiologi I Virusologi*, Medicina, Moscow, RU, No. 12, pp. 19-26 (1991).
DeJong, et al., "Drug delivery and nanoparticles: Applications and hazards," *International Journal of Nanomedicine*, 3(2):133-149 (2008).
Deng, et al., "Site-directed mutagenesis of virtually any plasmid by eliminating a unique site," *Anal. Biochem.*, 200:81-88 (1992).
Elvin, et al., "Protection against bubonic and pneumonic plague with a single dose microencapsulated sub-unit vaccine," *Vaccine*, 24:4433-4439 (2006).
Hinnebusch, et al, "Murine toxin of Yersinia pestis shows phospholipase D activity but is not required for virulence in mice," Int. J. Med. Microbiol., 290:483-487 (2000).
Jain, et al., "Chapter 1 Drug Delivery Systems—An Overview" *Methods in Molecular Biology*, 437:1-50.
Rudolph, et al., "Expression, Characterization, and Mutagenesis of the Yersinia pestis Murine Toxin, a Phospholipase D Superfamily Member," *The Journal of Biological Chemistry*, 274(17):11824-11831 (1999).
International Preliminary Report on Patentability in Application No. PCT/GB2008/003781 dated May 20, 2010.
Search and Examination Report in Application No. GB0820523.9 dated Mar. 13, 2009.
Search and Examination Report in Application No. GB0820523.9 dated Mar. 11, 2010.
Butler et al., "Experimental Yersinia pestis Infection in Rodents After Intragastric Inoculation and Ingestion of Bacteria", Infection and Immunity, vol. 36, No. 3, Jun. 1982, 1160-1167.
Cheng et al., "Effects of purification on the bioavailability of botulinum neurotoxin type A", Toxicology 249, 2008, 123-129.
Elsayed , "Oral Delivery of Insulin: Novel Approaches", Recent Advances in Novel Drug Carrier Systems, INTECH, Chapter 11, 2012, 282-314.
Morishita et al., "Is the oral route possible for peptide and protein drug delivery?", Drug Discovery Today, vol. 11, Nos. 19/20, Oct. 2006, 905-910.
Pang , "Modeling of Intestinal Drug Absorption: Roles of Transporters and Metabolic Enzymes (for the Gillette Review Series)", Drug Metabolism and Disposition, vol. 31, No. 12, 2003, 1507-1519.
Toutain et al., "Bioavailability and its assessment", J. vet. Pharmacol. Therap. 27, 2004, 455-466.

* cited by examiner

*Primary Examiner* — Gary Nickol
*Assistant Examiner* — Khatol Shahnan Shah
(74) *Attorney, Agent, or Firm* — Dean W. Russell; Jamie L. Graham; Kilpatrick Townsend & Stockton LLP

(57) ABSTRACT

The present invention relates to rodenticides, methods of killing a rodent comprising administering to said rodent, a lethal dose of an isolated *Yersinia* murine toxin polypeptide or an isolated antigenic analogue thereof, and methods of manufacturing novel rodenticides.

24 Claims, 4 Drawing Sheets

Fig.1.

SEQ ID NO:1 (*Yersinia* murine toxin polynucleotide sequence from KIM D27 strain)

ATGCTTCAAATAGATAATGTCATTAATAATATTGGAAACTACTTTCATCAT
CTAAGTAACATTAATTATATACGACTTCTGGATACCCCCATGCTTGGGGA
GCCCCATTTGGTAAAGAAATCATGCAGCAATCTTACTTACGGCAAGAGGA
GTTTGCAGGGGCAATGACTGAAGTACTGCGGAATTCGCGTTATCGCTGTG
ATATATCATCACTTAATAGCCCCGATGCAGAGTGGCGAAAAGTGATTTTT
AAGGCCATTGATGAATCCTTATCGAAAAAATGGGGCGAACTCAGCCAAC
TCAGTATAGGTTTCTTTTCGGCCAATCTCCAACAGTATTTATGAATGGGTT
ATCTGCTGCAACAAATGGCTCCCCTGACTTTGTTGCTTTTAAATCAGAGTT
AATTCAGCTAATTAAGGAGCGAGGACAATATTGGGAAAAAATGCCTGAA
ATTTGGCTAGGCCGTTTCTTTAGAATAGAAGAAGGGTTGGCTACATCATTT
ATGAGAAACGTGTATCCTGATTTCCCACCAATCAACGATACAAGAATGAC
ATGGAATCACACAAAAATAATGGCCTCAGATGGTACTGAAGCTCTTGTTG
GTGGACATAACATGAACATGGATCTATTTAGAAATTATCCACCTGTTCATG
ATGTATCAATTATCACTCATGGTTCTTCTGCTTATGGCTCCCAGCTATATCT
TAACGAACTATGGTCATGTAATTCAGATTTACTAAAAAAAGAATATTTTG
ATTATGAAAGCATGATGTGGGCGGTCGGAACAAAGTTCTATGATAAGCCT
GAAGATCCGCTTAAAAGCTCAGTTGCTATGAATTATATGAAGCAACGGCA
AGAGGACCTACTCAACTTGCATGAAACTTTAATCAGAAGGTAGCGACTC
GTATTAGTGAATACGAAAACATGGAAGAGTATAAAAAAGCAGACAGAGT
TTTATCAGTAGGTAAATATTGGACAGGACCTAATATGGAGCATGACTACC
AAAGAGGGTCTGAAATAATGAAAGAGCAACTGATAAAAAATGCTAAGCG
CATAATTAGAATTTCACAGCAAGATCTCGTGAGTGCTTGGAAAAAAAAAT
GGAAAGACCACTTTACGTGTAATTGGATTATTGAGGCTTTGTTAGAAAAT
AAAGATCTTCATATTCATGTTGTAGTCTCTGCTCTAGATGCAGCAGCTGGA
GCTGCTGGTGATCAGTACTCATTTGGTTCTGGAGCAGAACGGACCTATGA
ATTATTTAAGTATTACCTAACCCATGATATTGATACCGATGAAGTATTAGA
CGATCCTGATGGTAGCCGTGCTGATGCCTTAAAAAGAATATTGATTGCAC
CATTCTTCTTTACAGATAAAGTACCTGATGAAAATACAATTGAAGGCGAA
ACCTACAAGTGGCCTGATTTAGAACAAAGCGCTTATACTGCAACACTTAA
GCAAAAACCACTTTCGGAAAAACCCCCGCATCAAGGTATTATTGGTAGTG
CACTAATGTCAGCAATTAAAGGTAGTGGACTTTTCTATCCTAAAGTCCCTG
TTGCACCTGGTAATCACGCCAAATTAATGATTATTGACGATGAGTTGTACG
TTGTTGGATCAGATAATCTTTATCCCGGTTATCTGTCAGAGTTTGACTATTT
AGTCGAAGGAAAAGATGCAGTTAATGAATTAATGAAATCTTACTGGGAAC
CATTGTGGAAATATTCTAGCCCACATGCATTTCCAAAATTAAGCCCAAATT
AA

Fig.1(Cont).

SEQ ID NO:2 (*Yersinia* murine toxin polypeptide sequence from KIM D27 strain)

MLQIDNVINNIGNYFHHLSNINYIRLLDTPHAWGAPFGKEIMQQSYLRQEEFA
GAMTEVLRNSRYRCDISSLNSPDAEWRKVIFKAIDESLSKKMGRTQPTQYRFL
FGQSPTVFMNGLSAATNGSPDFVAFKSELIQLIKERGQYWEKMPEIWLGRFFR
IEEGLATSFMRNVYPDFPPINDTRMTWNHTKIMASDGTEALVGGHNMNMDL
FRNYPPVHDVSIITHGSSAYGSQLYLNELWSCNSDLLKKEYFDYESMMWAVG
TKFYDKPEDPLKSSVAMNYMKQRQEDLLNLHENFNQKVATRISEYENMEEY
KKADRVLSVGKYWTGPNMEHDYQRGSEIMKEQLIKNAKRIIRISQQDLVSAW
KKKWKDHFTCNWIIEALLENKDLHIHVVVSALDAAAGAAGDQYSFGSGAER
TYELFKYYLTHDIDTDEVLDDPDGSRADALKRILIAPFFFTDKVPDENTIEGET
YKWPDLEQSAYTATLKQKPLSEKPPHQGIIGSALMSAIKGSGLFYPKVPVAPG
NHAKLMIIDDELYVVGSDNLYPGYLSEFDYLVEGKDAVNELMKSYWEPLWK
YSSPHAFPKLSPN

SEQ ID NO:3 (forward primer)
CGGGATCCTAATGCTTCAAATAGATAA

SEQ ID NO:4 (reverse primer)
GTCCTCGAGTTAATTTGGGCTTAATTTTGG

SEQ ID No 5. (Forward priner)
GTCATGCATATGCTTCAAATAGATAATCTCA

SEQ ID No. 6 (Reverse primer)
GTCGGATCCTTAATTTGGGCTTAATTTTGG

SEQ ID No. 7 (Forward primer 2)
GACGTCGACTTAGTGATGGTGATGGTGATGATTTGGGCTTAATTTTGGAA

Fig.2.

![Gel image with lanes 1-8, markers at 94kDa, 67kDa, 43kDa, 30kDa, 20kDa; arrow to lane 7 labeled "Recombinant Murine toxin"]

Fig.3.

![Gel image with lanes 1-8, markers at 94kDa, 67kDa, 43kDa, 30kDa, 20kDa; arrow to lane 7 labeled "Recombinant Murine toxin"]

Fig.4.

94kDa
67kDa
43kDa
30kDa
20kDa

← Recombinant Murine toxin

← Cleaved GST-tag 1  2  3  4  5  6

Fig.5.

94kDa
67kDa
43kDa
30kDa
20kDa

← Recombinant Murine toxin 1  2  3  4

RODENTICIDE

CROSS-REFERENCE TO RELATED APPLICATIONS

This application is the U.S. national phase of International Application No. PCT/GB2008/003781 filed on Nov. 10,2008 and published in English on May 14,2009 as International Publication No. WO 2009/060225 A2, which application claims priority to Great Britain Patent Application No. 0721937.1 filed on Nov. 8, 2007, the contents of both of which are incorporated herein by reference.

BACKGROUND

This invention relates to novel rodenticides, methods of killing rodents and methods of manufacturing novel rodenticides.

Rodents have long been considered to pose a significant problem to human health, property and crops. The rat, alone, is known to carry nearly 70 diseases, many of which are transmittable to humans, including bubonic plague, typhus and leptospirosis. Meanwhile, farmers struggle to protect their crops from rodents and it has been estimated that probably 10% of the world's food supply is consumed or damaged by rats.

Governments in developed and developing countries are concerned that the risk from rodents has increased significantly in recent years given the recent rodent population explosion, working on the premise that an increased number of rodents means an increased risk to humans from such rodents. The rodent population explosion is thought to be the culmination of various factors such as the increasing number of mild and wet winters, the increasing availability of food litter in towns, and the increasing incidences of rodent resistance to known rodenticides.

The need for new rodenticides and methods of killing rodents, therefore, has never been greater. The present invention provides a new class of rodenticides.

Known rodenticides tend to be classified either as acute or chronic based on their mode of action. The chronic type, commonly known as anticoagulants, dominates the pest control market with approximately 95% of all rodenticides used belonging to this group. Warfarin is such an anticoagulant.

Rodent resistance to anticoagulants is increasing. As a result, other rodenticides are having to be used to control these resistant "super-rats". The drawback of many of these alternative rodenticides is that they tend to be potent not only to rodents, but also to non-target species such as pets, livestock and even humans. The most potent second-generation anticoagulants, for example, may only be used inside buildings so as to limit exposure of non-target animals. Two non-anticoagulant rodenticides are also available but guidelines limit repeat applications to 6 monthly intervals. The present invention provides a new class of rodenticide that is able to kill rodents and which is particularly advantageous as it is effective against rats that are resistant to currently available rodenticides. Also, the new rodenticides according to this invention are non-toxic to humans, various pets and livestock thus reducing the risk of environmental harm as well as avoiding harm to those humans in frequent contact with the rodenticide such as workers in the pest control industry.

Other attempts to design a new generation of rodenticide include WO 2006/095128, which teaches a rodenticide comprising an antibody or an antibody fragment thereof that binds to an extracellular epitope of a protein expressed in a rodent. The described method is complex because the user has to first identify a candidate epitope before the antibody which is going to become part of the rodenticide can be made. Having made the antibody, the antibody then needs to be tested for efficacy. The user then needs to decide which fusion to attach to the antibody, for example, the antibody can be fused to a toxin or a contraceptive. Finally, the fusions are administered to the rodent, where hopefully, the antibody part of the fusion can target the whole molecule to the appropriate place in the rodent.

The present invention does not require the step of having to make an antibody or an antibody fragment. The present invention does not even require the user to have to identify an epitope of a protein expressed in a rodent. The present invention therefore provides a far simpler method of producing a rodenticide. The present invention does not relate to an epitope that is expressed in a rodent. Instead, it relates to a toxin that is not natively found in a rodent because it is found in *Yersinia pestis*.

BRIEF DESCRIPTION OF THE DRAWINGS

FIG. 1 *Yersinia* murine toxin polynucleotide, polypeptide sequence and primer sequences.

FIG. 2 A 10-15% SDS PAGE Phastgel showing purified GST-tagged recombinant murine toxin CO92 species. Lanes (1) and (8) contain low molecular weight markers, lanes (2)-(5) are column flow through fractions and lanes (6) and (7) contains proteins eluted from the GSTrap column. The GST-tagged recombinant murine toxin (present in lanes 6 and 7) has a predicted molecular weight of ~93.5 kDa.

FIG. 3 A 10-15% SDS PAGE Phastgel purified GST-tagged recombinant murine toxin KIM species. Lanes (1) and (8) contain low molecular weight markers, lanes (2) -(5) are column flow through fractions and lanes (6) and (7) contains proteins eluted from the GSTrap column. The GST-tagged recombinant murine toxin (present in lanes 6 and 7) has a predicted molecular weight of ~93.5kDa FIG. 4 A 10-15% SDS PAGE Phastgel showing purified recombinant murine toxin CO92 and KIM species without the GST-tag. Lanes (1) and (6) contain low molecular weight markers. Lanes (2) and (3) contain samples of recombinant murine toxin CO92 species. Lanes (4) and (5) contain cleaved samples of recombinant murine toxin KIM species. Both the CO92 and the KIM species of recombinant murine toxin have a molecular weight of ~67.5 kDa. The removed GST-tag has a molecular weight of ~26 kDa.

FIG. 5. A 10-15% SDS PAGE Phastgel showing purified recombinant murine toxin CO92 and KIM species with a C-terminal HIS-tag. Lane 1 contains low molecular weight markers. Lanes (2) and (3) contain samples of recombinant murine toxin CO92 species. Lanes (4) contains samples of recombinant murine toxin KIM species. Both the CO92 and the KIM species of recombinant murine toxin have a molecular weight of ~67.5 kDa.

DETAILED DESCRIPTION OF THE INVENTION

Pest control is of primary importance in most societies. However, the increasing incidence of rodent resistance to known rodenticides makes controlling rodent populations more and more difficult.

*Yersinia pestis* is the causative agent of plague. Rodents play a part in the life cycle of this bacterium by becoming infected via a flea vector, dying and then becoming the source of infectious material for further insects to feed upon and spread disease.

As well as killing rats, Yersinia pestis is also known to be lethal to humans and it is this latter effect that has spurred research into its biology in the hope that such research could lead to a vaccine or cure for plague. Beginning in the late 1940s, work on plague toxins has yielded interesting insights into the pathogen.

One such insight is that Yersinia pestis harbours a plasmid (pMT1) that is not present in any other Yersinia species. Characterization of the plasmid led to the finding that Yersinia murine toxin (Ymt), a virulence factor, is encoded by this plasmid.

Virulence factors in general are prime candidates for new vaccines as they are likely to initiate an immune response in the host organism. They also tend to be targets for therapeutic drugs. Drug and vaccine research sometimes involves experimentation on rats and mice in order to assess the efficacy of the drug or vaccine candidate or the animal may be required as the source of antibodies against the virulence factor.

Unfortunately, sometimes a rodent may die as a result of being administered the drug or, if it is a vaccine being tested, and that vaccine is not effective, then the rodent could die from the disease against which the vaccine is meant to protect. In the case of Ymt, mice and rats have been administered with this toxin in order to observe the role of this toxin in plague infection and also to see whether there were any immunizing effects.

Killing the rat or mouse, however, was never the intention of the experiments per se, rather, death of the animal was an unfortunate outcome of carrying out the experiment. There is no suggestion in the reports of this research that the killing of the mouse or rat is a useful outcome, that is, that it would be practical to use Ymt as a rodenticide. This is particularly so given that the method of administration of Ymt to the rats or mice in these publications is by injection, not a particularly practical method for a rodenticide since any such method would have to first involve trapping the rodent and then injecting each rodent by hand.

The inventors have found that Ymt can be harnessed in a form that can be administered without injection and deployed to selectively kill rodents. In a first aspect of the invention, therefore, there is provided a method of killing a rodent comprising administering to said rodent, a lethal dose of isolated Ymt polypeptide or an isolated antigenic analogue thereof, other than by direct injection.

Methods of administration other than by direct injection include, but are not limited to oral, rectal, transmucoal, transnasal, pulmonary, and transdermal/topical administration. Such methods for administration are well known in the art (e.g. Jain et al., Methods in Molecular Biology, vol 437, pages 1-50; De Jong et al., International Journal of Nanomedicine 2008: 3(2) 133-149 which are herein incorporated by reference) and can be readily applied to the present invention. Preferably, the method of administration is oral administration. More preferably, the Ymt or its antigenic analogue is delivered in a feed (e.g. mixed with cereals such as oats). The feed may additionally comprise protease inhibitors to prevent degradation of the Ymt or its antigenic analogue once it reaches the rodent's stomach and/or the gastro-intestinal tract. Further, a carrier may also be included in a feed wherein the carrier is a substance that helps delivery of Ymt or its antigenic analogue through the rodent's gut or stomach wall into the bloodstream.

Alternatively, the Ymt or its antigenic analogue can be administered orally without the feed, but may still include a protease inhibitor and/or a carrier.

By "rodent" is meant any small placental mammal that belong to the order Rodentia, including but not limited to rats and mice.

Preferably, the rodent being killed is a rat. More preferably, the rodent being killed is of the species Rattus rattus or Rattus norvegicus.

By "isolated Ymt" is meant that that the Ymt is not present in the form of a naturally occurring Yersinia pestis organism. By "Ymt" is meant a polypeptide comprising the sequence of SEQ ID NO:2.

"Antigenic analogue" as used with respect to a polypeptide, describes any polypeptide that is capable of killing a rodent in a similar dose dependence as isolated Ymt polypeptide and shares more than 60% identity or similarity with SEQ ID NO:2. Preferably the antigenic analogue sequence shares more than 65, 70, 75, 80, 85, 86, 87, 88, 89, 90, 91, 92, 93, 94, 95, 96, 97, 98, 99% identity or similarity with SEQ ID NO:2.

Although the degree of dose dependent activity need not be identical to that of Ymt comprising SEQ ID NO:2, preferably the "antigenic analogue" will exhibit similar dose-dependence in a given activity assay compared to Ymt comprising SEQ ID NO:2. "Similar dose-dependence" means that the assay results are not significantly different as measured by at least one statistical test that is appropriate to the assay e.g. the student-T test.

The "antigenic analogue" may be a polypeptide that is homologous or analogous to sequence of SEQ ID NO:2. The two terms "homologous" and "analogous" as used herein, are used interchangeably. Two polypeptides are said to be "homologous" or "analogous", if the sequence of one of the polypeptides has a high enough degree of identity or similarity to the sequence of the other polypeptide, that is, they share more than 60, 65, 70, 75, 80, 85, 90 or 95%. "Identity", when referring to a polypeptide, indicates that at any particular position in the aligned sequences, the amino acid residue is identical between the sequences. "Similarity", when referring to a polypeptide, indicates that, at any particular position in the aligned sequences, the amino acid residue is of a similar type between the sequences. For example, amino acid residues can be grouped by their side chains. Glycine, alanine, valine, leucine and isoleucine all have aliphatic side-chains and amino acids in this group may be regarded as similar. Proline, although a cyclic amino acid, shares many properties with the aliphatic amino acids and may also be regarded as being grouped with the other aliphatic amino acids. Another group is the hydroxyl or sulphur containing side chain amino acids. These are serine, cysteine, threonine and methionine.

Phenylalanine, tyrosine and tryptophan are grouped together as the aromatic amino acids. Histidine, lysine and arginine are the basic amino acids. Aspartic acid and glutamic acid are the acidic amino acids and asparagine and glutamine are their respective amides. Also included in these groups are modified amino acids (i.e. non-naturally occurring amino acids) that have side-chains that share similar properties with the naturally occurring amino acids. Members of a particular group can be regarded as being "similar". Swapping one amino acid from a group with another amino acid from the same group is often termed a conservative substitution.

The definition of a "homologous" or "analogous" polypeptide may also include a polypeptide that has had one or more amino acids deleted or inserted into the sequence, as long as the overall identity or similarity is more than 60, 65, 70, 75, 80, 85, 90 or 95%. The amino acids that are inserted or substituted may be non-conservative amino acid changes as long as the overall identity or similarity falls within the given percentages. Homologous or analogous polypeptides may include natural biological variants.

Degrees of identity and similarity can be readily calculated using known computer programs (see Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). For example, simple sequence comparisons can be done on web-sites such as the NCBI website: http://www.ncbi.nlm.nih.gov/BLAST/(version 2.2.11). As used herein, percentages identity or similarities between sequences are measured according to the default BLAST parameters, version 2.2.11. For polypeptides, blastp is used with the following settings: advanced blasting, low complexity, expect 10, word size 3, blosun 62 matrix, existence: 11, extension: 1 gap costs, inclusion threshold 0.005 and alignment view: hit table. For nucleotide blasting, blastn is used, with low complexity, expect 10, wordsize 11, alignment view: hitable, semi-auto and autoformat.

"Antigenic analogues" also includes a fragment or fragments of Ymt polypeptide comprising SEQ ID NO:2 provided the fragment or fragments kills the rodent to which it is administered and shares at least one antigenic determinant with SEQ ID NO:2. Two polypeptides share the same antigenic determinant if they both bind to a particular antibody with similar binding affinities or are recognized by the same T cell in conjunction with class I or class II major histocompatibility antigens. Assays for recognition by T cells include chromium release assays, ELISPOT assays and proliferation assays and are well known in the art. Techniques for measuring the binding affinities of proteins with proteins are well known in the art and may include filter binding studies, ELISAs (see example 5) or chromatography. Binding affinities are regarded as being similar when they are statistically significant using the T-test or student T test.

Such fragments may form part of a larger polypeptide as long as the fragment forms a single continuous region. Several fragments may be comprised within a single larger polypeptide.

An "antigenic analogue" may include combinations of the above mentioned variations, that is to say, the antigenic analogue polypeptide may comprise any combination of a deletion, addition of a fragment, a substitution and/or a insertion, as long as it has similar binding affinities compared to a polypeptide comprising the sequence SEQ ID NO:2 and kills the rodent to which it is administered. Such deletions, additions, substitutions and insertions may be naturally occurring or deliberately engineered.

Methods of making synthetic antigenically equivalent polypeptides are well known in the art and include techniques such as site-directed mutagenesis (see Deng, W. P. and Nickoloff, T. A., Anal. Biochem. 200, 81-88 (1982)), polymerase chain reaction, chemical gene synthesis and chemical polypeptide synthesis.

Preferably, the isolated Ymt is recombinant Ymt. "Recombinant Ymt" is defined as Ymt that is expressed as a heterologous gene. More preferably, the isolated Ymt is expressed in *Escherichia coli*.

"Lethal dose" can mean a single administration that proves lethal or it can also mean more than one administration, if this leads to the killing of the rodent, i.e. the Ymt poisoning can be accumulative.

In a second aspect of the invention, there is provided a method of controlling rodent populations comprising administering to one or more rodents, a non-injected lethal dose of isolated Ymt polypeptide or an antigenic analogue thereof.

Ymt is particularly suited in its use for killing rodents or controlling rodent populations for a number of reasons. First, it has been found that Ymt displays specificity in its toxicity; rabbits, dogs and chimpanzees are less susceptible to this toxin compared to rats and mice. Such specificity is useful in a rodenticide as it avoids unintentional poisoning of humans, particularly those working in the pest control industry. Non-rodent pets and livestock will also be safe from unintentional dosing, as will any non-rodent wild-life.

Second, unlike warfarin (another rodent-specific rodenticide), there are no major problems with resistance against Ymt in wild rodent populations to date. In addition, because Ymt is a biological molecule with demonstrated phospholipase and β-adrenergic blocking agent activity, it will be more difficult for a rodent to develop resistance since its mode of action in a rodent is likely to be more complex than that of the synthesized chemicals used in current rodenticides. Also, Ymt has been honed by evolution to kill rats since it is advantageous for *Yersinia pestis* to kill the rodent it has infected in order to release a source of infectious material which aids further spread of the disease. This again suggests that Ymt is going to be difficult for a rat to build up resistance against.

In a third aspect of the invention, there is provided a rodenticide comprising isolated Ymt polypeptide or an isolated antigenic analogue thereof.

"Ymt" and "Ymt polypeptide" are used interchangeably in this application except for where there is mention of the Ymt gene or any polynucleotide encoding the Ymt polypeptide. Also, where Ymt, Ymt polypeptide, or their antigenic analogues thereof are mentioned in this application, preferably, they are not fused to an antibody or antibody fragment.

By "rodenticide" is meant any composition that is lethal to a rodent when administered in sufficient quantity. Preferably, the rodenticide is lethal to rats. More preferably, the rodenticide is lethal to rats of the species *Rattus rattus* or *Rattus norvegicus*.

In one embodiment of the third aspect of the invention, the isolated Ymt polypeptide or isolated antigenic analogue thereof, is a recombinant Ymt polypeptide or a recombant antigenic analogue thereof. Previous studies on mice and rats have been carried out with Ymt purified from the actual *Yersinia pestis* organism. Using such a dangerous pathogen as *Yersinia pestis* in laboratory requires a high level of containment and there are many restrictions on how such studies are to be carried out. Recombinant *Yersinia pestis*, however, would negate the need for high levels of containment as viable *Yersinia pestis* organisms would no longer be present since the Ymt is being produced in a safer organism such as *Escherichia coli*. This is particularly important for the large-scale production of Ymt necessary for manufacture of the rodenticide.

In a further aspect of the invention, there is provided an expression plasmid comprising a polynucleotide sequence that encodes Ymt polypeptide, or an antigenic analogue thereof. One example of a polynucleotide sequence encoding the Ymt polypeptide is given in SEQ ID NO:1. Preferably, the polynucleotide sequence is codon-optimised for improved expression in the expression organism. e.g. the polynucleotide will be codon-optimised for expression of Ymt in an *Escherichia coli* host organism. In one embodiment, the expression plasmid further encodes a tag which is attached to the Ymt polypeptide or antigenic analogue thereof. Such tags can stabilise the polypeptide and/or aid purification. Preferably, the tag is a GST or a Histidine (HIS) tag. More preferably, the tag is a HIS tag. In another aspect of the invention, there is provided a bacterium that expresses Ymt polypeptide or an antigenic analogue thereof wherein the bacterium is not *Yersinia pestis*. Preferably, the bacterium is *Escherichia coli*.

In a fourth aspect of the invention, there is provided isolated Ymt polypeptide or an isolated antigenic analogue thereof, suitable for use in controlling rodent populations. Preferably, the isolated Ymt polypeptide or isolated antigenic analogue thereof is a recombinant Ymt polypeptide or recombinant antigenic analogue thereof. In a fifth aspect of the invention, there is provided the use of Ymt polypeptide or its antigenic analogue as a rodenticide. Preferably, the Ymt polypeptide or its antigenic analogue is a recombinant polypeptide or a recombinant antigenic analogue thereof. Having a recombinant polypeptide rather than having to purify the toxin from the original organism is advantageous for the reasons already stated above, namely, that it takes away the need for high level containment in the production process. More preferably, the recombinant polypeptide or recombinant antigenic analogue is produced in a safer organism such as *Escherichia coli*.

In one embodiment of the fifth aspect of the invention, the Ymt polypeptide or its antigenic analogue is attached to a polypeptide tag. Preferably, the polypeptide tag enables easier purification. More preferably, the polypeptide tag is a GST tag or a HIS tag. Most preferably, the polypeptide tag is a HIS tag for it has been found that the presence of a HIS tag does not interfere with the toxic properties of the Ymt polypeptide when the polypeptide is being used as a rodenticide. The absence of a requirement to remove the tag before the Ymt polypeptide or its antigenic analogue is used as a rodenticide saves time and effort in the production of the rodenticide. The His tag can be fused to either the N-terminal or the C-terminal end of the Ymt polypeptide or its antigenic analogue. In one embodiment, the His tag is fused to the C-terminal end of the Ymt polypeptide or its antigenic analogue.

Rats are unable to vomit to get rid of toxic substances. This is potentially a fatal problem for the rat if the food is poisonous. Rats have therefore adapted their behaviour to minimise the risk of being poisoned so that when a rat finds new food, it will only eat a little and wait to see whether it falls ill. If it does fall ill, it will avoid that food for the rest of its life. This is often referred to as "bait avoidance" or "bait shyness".

One aspect of the present invention enables bypassing of bait avoidance by microencapsulating the Ymt or antigenic analogue thereof in a microcapsule that delays release of the polypeptide or releases the polypeptide at a rate slow enough (at least initially) to not trigger the bait avoidance mechanism in the rat.

In a sixth aspect of the invention, therefore, there is provided a microcapsule comprising Ymt polypeptide or an antigenic analogue thereof, and microencapsulation material.

In one embodiment of the sixth aspect of the invention, the Ymt polypeptide or antigenic analogue thereof is enclosed in the microcapsule. In another embodiment, the Ymt polypeptide or antigenic analogue thereof is embedded in the membrane or matrix of the microcapsule, or partially embedded in the membrane or matrix. In a further embodiment, there is a mixture of locations of the Ymt polypeptide or antigenic analogue thereof in a single microcapsule so that some of the Ymt polypeptide or antigenic analogue thereof is enclosed inside the microcapsule whereas other Ymt polypeptide or antigenic analogue particles are embedded or partially embedded in the microcapsule membrane or matrix. By "partially embedded" is meant that Ymt polypeptide or antigenic analogue thereof is contacting the microcapsule membrane or matrix in any way that restricts it from freely floating away from the membrane or matrix.

Encapsulation methods suitable for this invention are known in the art (see for example, Elvin et al., 2006, Vaccine, 24, 4433-4439 including but not restricted to liposome formation. Such methods may include the method set out in example 1. The formulation may be adjusted to better suit the delivery of Ymt polypeptide or antigenic analogues thereof. Such fine-tuning can be carried out by routine experimentation using known methods including but not restricted to those set out in WO 00/56282, WO 00/56361, WO 00/56362 and JP3145405.

In one embodiment of the sixth aspect of the invention, the microencapsulation material is biodegradable. By "biodegradable" is meant that the material is degradable by a rodent's metabolism e.g. by enzymes found in the rodent. The degradation of the microencapsulation material enables the Ymt polypeptide or antigenic analogues thereof to become available in the rodent's body and thus exhibit its effect on the rodent. An example of a biodegradable microencapsulation material is poly-(L-lactide) or PLA or poly (lactic/glycolic acid) PGLA.

Preferably, the microcapsulation material of the sixth aspect of the invention enables slow or delayed release of the Ymt polypeptide or antigenic analogue thereof into a rodent's body. Such encapsulation materials (e.g. gelatin) are well known in the art of health-foods e.g. vitamin supplements etc and could be readily adapted by a skilled person for the present invention.

In a seventh aspect of the invention, there is provided rodent edible food comprising one or more microcapsules of the sixth aspect. The terms "rodent edible food" and "feed" are used interchangeably in this application.

The microcapsule will also help protect the Ymt polypeptide or antigenic analogue thereof from degradation in the rodent's stomach and facilitate uptake in the gut, thus increasing the chances of successful delivery of complete Ymt polypeptide or antigenic analogue thereof into the rodent's system instead of being destroyed by the stomach enzymes and excreted.

Preferably, the rodent edible food is rat edible food.

Alternatively to adding microcapsules to rodent-edible food, the microcapsule of the sixth aspect of the invention can be in an aerosol spray which the rodent would inhale. This would bypass the stomach degradative enzymes and thus increase the probability of intact Ymt polypeptide or antigenic analogue thereof being delivered into the rodent's system.

In an eighth aspect of the invention, therefore, there is provided an aerosol container comprising the microcapsules of the sixth aspect or the rodenticide of the third aspect of the invention. Suitable aerosol containers for dispensing microcapsules of the present invention are well known in the art (see for example, FR2685857).

In a ninth aspect of the invention, there is provided a housing container suitable for trapping a rodent or rodents, wherein the rodenticide of the third aspect, the microcapsule of the sixth aspect of the invention, the rodent edible food of the seventh aspect of the invention or the aerosol container of the eighth aspect of the invention is housed therein. Examples of rat traps that may be modified to suit the present invention include humane live traps that have automatic locking doors that can be tripped as the animal enters (see for example, those traps described on www.pestproducts.com/chipmunk_trap.htm). In a preferred embodiment for where the housing container comprises an aerosol container of the eighth aspect of the invention, the housing container suitable for trapping the rodent or rodents is relatively air-tight in order that the aerosol is not dispersed into the atmosphere surrounding the trap. This would decrease the over all amount of aerosol needed to be dispensed in order to kill the rodent.

Where the housing container houses an aerosol container, the housing container also comprises a mechanism that releases a lethal dose of aerosol spray into the housing container that is triggered upon entry of a rodent into the housing container (e.g. by the pressure exerted by the rodent's weight) .Such a mechanism can be a modification of the mechanism that closes the doors on entry of a rodent so that the modified mechanism both closes the door to the trap and releases the aerosol spray upon triggering.

In an alternative embodiment, instead of a housing container housing an aerosol container, the housing container can be modified for other forms of toxin delivery. For example, the housing container could contain an apparatus suitable for needleless delivery, such as a mat comprising microstructures that are more typically associated with transdermal delivery (e.g. the solid microstructured transdermal system of 3M). The delivery of the Ymt or its antigenic analogue would then occur by the rodent contacting the mat with its paws or underbelly. It is also possible that the housing container may just have the Ymt or its antigenic analogue in solid form dispersed on the floor of the container. The rodent will then come into contact with the toxin or its antigenic analogue as it enters the container. The toxin or its antigenic analogue will be ingested as the rodent licks its paws.

Also contemplated by the inventors are rodenticide kits. Thus, in a tenth aspect of the invention, there is provided a kit comprising Ymt polypeptide or an antigenic analogue thereof and a housing container suitable for trapping a rodent or rodents. Preferably, the kit comprises the Ymt polypeptide or antigenic analogue thereof in an aerosol form. More preferably, the Ymt polypeptide or antigenic analogue thereof is in a microcapsule form of the sixth aspect of the invention. Even more preferably, the housing container comprises a mechanism that can release a lethal dose of aerosol spray into the housing container and is triggered upon entry of a rodent into the housing container.

Alternatively, the kit comprises the Ymt polypeptide or an antigenic analogue thereof in a form suitable for applying to surfaces with an applicator e.g. a liquid or emulsion form. The applicant may be in the form of a brush. By applying the Ymt polypeptide or antigenic analogue thereof to surfaces such as wire sheaths, cables, pipes or construction parts, this could protect such surfaces from continued gnawing by the rodents.

In a tenth aspect of the invention, there is provided a method of making recombinant Ymt or its antigenic analogue comprising the steps of:
 a) putting a polynucleotide encoding the Ymt or its antigenic analogue in an expression plasmid;
 b) transforming the expression plasmid into an expression host organism;
 c) expressing the Ymt or its antigenic analogue in the expression host organism; and
 d) purifying the Ymt or its antigenic analogue.

Preferably, the expression host organism is a bacterium. More preferably, the expression host organism is *Escherichia coli*.

Preferably, the expression plasmid additionally encodes a polypeptide tag that is attached to the Ymt or its antigenic analogue. More preferably, that polypeptide tag enables easier purification. Examples of suitable polypeptide tags are a GST tag or a HIS tag. Where the polypeptide tag is a HIS tag, the tag is preferably attached at the C-terminal end of the Ymt or its antigenic analogue.

In a particular embodiment, the method of the tenth aspect of the invention additionally comprises the step of cleaving the tag after purification has taken place. More preferably, the cleavage step uses Factor Xa™, Thrombin or Precission™ where the tag is a GST tag.

It has been found that the presence of a HIS tag does not affect the rodenticidal properties of the Ymt to such an extent that it no longer functions. As such, it is preferred that a HIS tag is used since no cleavage step is required to remove the HIS tag before administration to the rodent. In one embodiment of the tenth aspect of the invention, where the His tag is used, the method does not include cleaving the tag after purification has taken place.

EXAMPLES

Example 1 Cloning of Ymt with a GST Tag into an *Escherichia coli* Expression System The gene encoding Ymt was amplified from template DNA that had been extracted from *Yersinia pestis* strain CO92 or KIM D27. Taq polymerase (Roche Ltd) was used to amplify the DNA of interest using the polymerase chain reaction (PCR). The forward primer used consisted of the sequence shown in SEQ ID NO:3 and the reverse primer used consisted of the sequence shown in SEQ ID NO:4.

The PCR product was then cloned into a plasmid vector of the pGEX series (pGex-5X-1, GE Healthcare) via the BamHI and XhoI cloning sites. The pGEX-Ymt construct was then transformed into *Escherichia coli* strain JM109 (Promega). The Ymt gene from both the CO92 and the KIM D27 strains of *Y. pestis* were cloned using this procedure.

Example 2 Cloning of the Ymt Gene with a HIS Tag

Taq polymerase (Roche Ltd) was used to amplify the DNA of interest using the polymerase chain reaction (PCR). The forward primer used consisted of the sequence shown in SEQ ID NO:5 and the reverse primer used consisted of the sequence shown in SEQ ID NO:6.

The PCR product was then cloned into a plasmid vector of the pET series (pET22b, Novagen) via the NdeI and BamHI cloning sites. The pET-Ymt construct was then transformed into *E. coli* Rosetta-Gami (DE3) pLysS (Promega). The Ymt gene from both the CO92 and the KIM D27 strains of *Y. pestis* were cloned using this procedure.

Example 3 Production of Recombinant Toxin

A single colony was used to seed 100 ml of L-broth containing ampicillin (selecting for Amp resistance on the plasmid vector) and incubated at 37° C. with shaking at 180 rpm. The overnight cultures were used to seed larger volumes of prewarmed L-broth containing ampicillin and cultured at 37° C. for between 2-4 hrs reaching an optical density (OD600 nm) of approximately 0.4. The cultures were then cooled to 20° C. and the expression of recombinant murine toxin was induced by the addition of IPTG (up to 1 mM). The induced cultures were then incubated overnight at 20° C. with 180 rpm shaking. A pellet of bacteria was created via the centrifugation (10000 g for 15 mins at 4° C.) of the induced cultures and stored at −20° C.

The bacterial pellet was defrosted and resuspended in 20-40 ml of Phosphate Buffered Saline pH 7.2. The resuspension was then sonicated for three thirty second time periods (with thirty second time intervals on ice). The protein extract was then centrifuged at 10000 g for 15 mins and filtered (0.2 µm).

For the GST-tagged Ymt containing protein extracts, the filtered extract was then loaded onto a GSTrap FF (GE Healthcare) affinity column that purifies recombinant proteins with a Glutathione S Transferase tag. The GST-tagged recombinant murine toxin (both CO92 and KIM species) was successfully purified as per the manufacturers' instructions (FIGS. 2 and 3). By treating the tagged recombinant proteins overnight at room temperature with a protease (Factor Xa™ (supplied by GE Healthcare)) that cleaves off the GST-tag it was possible to produce an untagged version of murine toxin (FIG. 4).

For the His-tagged Ymt containing protein extract, the filtered extract was then loaded onto a HISTrap FF (GE Healthcare) affinity column that purifies recombinant proteins with a histidine tag. The HIS-tagged recombinant murine toxin (both CO92 and KIM species) was successfully purified as per the manufacturers' instructions (FIG. 5). The purified material was dialysed overnight into PBS pH7.2 for subsequent storage at $-20°$ C.

Example 4 Preparation of PLLA Encapsulated Ymt Polypeptide

Microspheres will be prepared using a modified solvent evaporation process. Freeze-dried recombinant Ymt (rYmt) (2 mg) is resuspended in 100 µl of distilled water prior to the addition of 100 µl of 5% (w/v) polyvinyl alcohol (PVA) to form a 2.5% PVA internal phase. The internal phase is then added to 2 ml of a 5% polymer solution (100 mg of poly-L-lactide (PLLA) in 2 ml dichloromethane) and sonicated on ice (60 W for 2 min) to form a water-in-oil primary emulsion. This is then added to 30 ml of 5% PVA and homogenised (Silverson) on ice (16,000 rpm for 8 min) to form a water-in-oil-in-water double emulsion. The microspheres are stirred overnight at room temperature to remove the solvent by the process of evaporation. Residual PVA and solvent are then removed by washing the microspheres. Briefly, the microspheres are centrifuged at 10,000 rpm (4° C.) for 20 min to form a pellet. The supernatant is removed and the pellet re-suspended in water. This washing step is performed twice. The final pellet is re-suspended in 2 ml water and freeze-dried for 48 h at $-20°$ C., followed by 2 h, $-80°$ C. condenser 0.007 µBarr using VITIS Advantage E1 freeze-dryer.

Example 5 Toxicity of Recombinant Ymt

The toxicity study may consist of a pre-test starvation period of up to 12 hours (this is optional, mice are not starved); the administration of a substance; and an observation period of up to 21 days. Doses are administered to groups of animals such that a dose-mortality curve, ranging from the highest dose that will effect 0% to the lowest dose that will effect 100% mortality, is obtained. The dose that effects 0% mortality acts as the control for the study. For comparative studies e.g. confirming resistant status, only 'spot-doses' will be used. The results of these 'spot-doses' are compared with an established standard dose-mortality curve.

Groups of up to 5 animals are weighed and, were possible, uniquely tailmarked. Prior to administration the dosing solutions are visually checked to confirm homogeneity and suitability for oral administration. If the homogeneity or suitability is suspect the solution will be returned to the originator for immediate replacement. No more than two groups of animals are ever tested at any one time. The initial study is to be completed and the results evaluated before adopting a step-wise approach to further "doses".

At time 0, substances are administered orally by gavage, or intraperitoneally, as a single dose. The dosing solution should be administered at the preferred rate of 1.0 ml per 1 kg bodyweight for rats (the maximum permissible rate is 5.0 ml per 1 kg bodyweight). The maximum permissible dose rate for mice is 10.0 ml per 1 kg bodyweight. Following oral dosing the animals are denied food and water for a further 0.5 hours.

Following administration the animals are maintained for up to a further 21 day observation period, with standard laboratory diet and water available ad lib. The animals are observed and symptoms recorded at least once a day. Any animal exhibiting symptoms of a severity which may be expected to effect death is culled by either $CO_2$ or cervical dislocation, and their body weight recorded. Animals so culled are recorded as dead on that day, or on one of the next two days, depending on the severity of the symptoms.

At the end of the observation period any survivors will be culled by $CO_2$ or cervical dislocation, and their body weight recorded.

The active toxicity (LD50) is derived from the log-probability regression of the amount of active ingredient administered against mortality.

Purified recombinant murine toxin was tested for its toxicity in vivo towards mice and rats via the method outlined above. Recombinant murine toxin was lethal to mice via the intraperitoneal route (Table 1). The toxin was also tested for its toxicity towards mice and rats following administration via the oral route. Recombinant murine toxin was found to be lethal for mice and rats following oral administration (Table 2).

TABLE 1

Overview of the toxicity of the recombinant murine toxin following administration to mice via the intraperitoneal route. The recombinant murine toxin produced with a GST tag was enzymically treated to cleave the tag from the toxin prior to administration to animals. The recombinant toxin produced with a HIS tag did not have this tag removed prior to administration to animals.

| Delivery method (Production method: GST or HIS) | Species of animal | Dose (µg/kilogram) | Numbers of animals | Mortality |
|---|---|---|---|---|
| IP (GST) | Mouse | 20.0 | 2 | 0/2 |
| IP (GST) | Mouse | 40.0 | 2 | 2/2 |
| IP (HIS) | Mouse | 20.0 | 2 | 1/2 |
| IP (HIS) | Mouse | 40.0 | 2 | 2/2 |

TABLE 2

Overview of the toxicity of the recombinant murine toxin following administration to mice via the oral route. The recombinant toxin used in these studies was produced with a HIS tag that was not removed prior to administration to animals.

| Material | Delivery method | Species of animal | Dose (µg/kilogram) | Numbers of animals | Mortality |
|---|---|---|---|---|---|
| Murine toxin | Oral | Mouse | 2500 | 2 | 1/2 |
| Murine toxin | Oral | Mouse | 5000 | 2 | 1/2 |
| Murine toxin | Oral | Mouse | 10000 | 2 | 2/2 |
| Murine toxin | Oral | Rat | 9900 | 2 | 1/2 |
| HIS tag* | Oral | Mouse | 6000 | 2 | 0/2 |

*The HIS tag control was a six histidine residue peptide that was chemically synthesised and is identical to the tag attached to murine toxin.

Example 6 Testing for Antigenic Analogues By Comparing Dose-dependent Activities Using ELISA Each well of a 96-well flat-bottomed microtitre plate is to be coated by application of 50 µl of Ymt polypeptide at 3-5 µg/ml in carbonate/bicarbonate coating buffer (Sigma). Excess binding capacity is adsorbed by overnight incubation at 4° C. with phosphate-buffered saline (PBS) supplemented with 2% (w/v) non-fat milk powder. Prior to each additional step plates are washed 3× with PBS supplemented with 0.05% (v/v) tween-20 (PBS-T). Wells are probed with an appropriate antibody in a serial dilution followed by application of an appropriate biotin conjugated second-step antibody, followed by a streptavidin-HRP (horseradish peroxidase) conjugate and finally visualised with ABTS reagent (Sigma) dissolved in phosphate/citrate buffer (Sigma) supplemented at 50 µl/100 ml with 30% $H_2O_2$.

Quantitative values are determined by spectrophotometry at 405 nm. The procedure is then repeated but replacing the polypeptide of the invention with a putative antigenic analogue. If the dose-dependence activities are deemed similar by at least one statistical test that is appropriate, then the putative antigenic analogue is considered to be an antigenic analogue of the invention. This method can be varied to suit the particular circumstances of the assay. For example, it may be more convenient to have the wells coated with the antibody and then probed with the putative antigenic analogue. The variations will be well known to a person skilled in the art.

The invention claimed is:

1. A method of killing a rodent, comprising administering to the rodent a lethal dose of isolated *Yersinia* murine toxin polypeptide or an isolated antigenic analogue thereof, wherein the *Yersinia* murine toxin polypeptide or the isolated antigenic analogue thereof is administered in a feed, and wherein administration of the *Yersinia* murine toxin polypeptide or isolated antigenic analogue thereof in the feed kills the rodent to which it is administered
   wherein the isolated antigenic analogue is a polypeptide that is capable of killing a rodent in a similar dose dependence as isolated *Yersinia* murine toxin polypeptide and shares more than 60% identity or similarity with SEQ ID NO:2.

2. The method of claim 1, wherein the rodent is a rat.

3. The method of claim 2, wherein the rat is of the species *Rattus rattus* or *Rattus norvegicus*.

4. The method of claim 1, wherein the isolated *Yersinia* murine toxin polypeptide or the isolated antigenic analogue thereof is a recombinant *Yersinia* murine toxin polypeptide or a recombinant antigenic analogue thereof.

5. The method of claim 1, wherein the *Yersinia* murine toxin polypeptide or the isolated antigenic analogue is administered in the presence of one or more protease inhibitors.

6. The method of claim 1, wherein the *Yersinia* murine toxin polypeptide or the isolated antigenic analogue additionally comprises a HIS tag.

7. The method of claim 1, wherein the isolated *Yersinia* murine toxin polypeptide or the isolated antigenic analogue thereof is a recombinant *Yersinia* murine toxin or its antigenic analogue obtained by a method comprising the steps of:
   putting a polynucleotide encoding the *Yersinia* murine toxin or its antigenic analogue in an expression plasmid;
   transforming the expression plasmid into an expression host organism;
   expressing the *Yersinia* murine toxin or its antigenic analogue in the expression host organism; and
   purifying the *Yersinia* murine toxin or its antigenic analogue.

8. The method of claim 7, wherein the expression plasmid additionally encodes a polypeptide tag that is attached to the *Yersinia* murine toxin or its antigenic analogue.

9. The method of claim 8, wherein the polypeptide tag is a GST or HIS tag.

10. The method of claim 9, wherein the polypeptide tag is a HIS tag.

11. The method of claim 8, wherein the method additionally comprises the step of cleaving the tag after purification has taken place.

12. A method of killing a rodent comprising administering to the rodent a lethal dose of isolated *Yersinia* murine toxin polypeptide or an isolated antigenic analogue thereof, wherein the *Yersinia* murine toxin polypeptide or the isolated antigenic analogue thereof is administered by oral administration, and wherein oral administration of the *Yersinia* murine toxin polypeptide or isolated antigenic analogue thereof kills the rodent to which it is administered
   wherein the isolated antigenic analogue is a polypeptide that is capable of killing a rodent in a similar dose dependence as isolated *Yersinia* murine toxin polypeptide and shares more than 60% identity or similarity with SEQ ID NO:2.

13. The method of claim 12, wherein the rodent is a rat.

14. The method of claim 13, wherein the rat is of the species *Rattus rattus* or *Rattus norvegicus*.

15. The method of claim 12, wherein the isolated *Yersinia* murine toxin polypeptide or the isolated antigenic analogue thereof is a recombinant *Yersinia* murine toxin polypeptide or a recombinant antigenic analogue thereof.

16. The method of claim 12, wherein the *Yersinia* murine toxin polypeptide or the isolated antigenic analogue is administered in the presence of one or more protease inhibitors.

17. The method of claim 12, wherein the *Yersinia* murine toxin polypeptide or the isolated antigenic analogue additionally comprises a HIS tag.

18. The method of claim 12, wherein the isolated *Yersinia* murine toxin polypeptide or the isolated antigenic analogue thereof is a recombinant *Yersinia* murine toxin or its antigenic analogue obtained by a method comprising the steps of:
- putting a polynucleotide encoding the *Yersinia* murine toxin or its antigenic analogue in an expression plasmid;
- transforming the expression plasmid into an expression host organism;
- expressing the *Yersinia* murine toxin or its antigenic analogue in the expression host organism; and
- purifying the *Yersinia* murine toxin or its antigenic analogue.

19. The method of claim 18, wherein the expression plasmid additionally encodes a polypeptide tag that is attached to the *Yersinia* murine toxin or its antigenic analogue.

20. The method of claim 19, wherein the polypeptide tag is a GST or HIS tag.

21. The method of claim 20, wherein the polypeptide tag is a HIS tag.

22. The method of claim 18, wherein the method additionally comprises the step of cleaving the tag after purification has taken place.

23. The method of claim 1, wherein the isolated antigenic analogue shares more than 90% identity or similarity with SEQ ID NO:2.

24. The method of claim 12, wherein the isolated antigenic analogue shares more than 90% identity or similarity with SEQ ID NO:2.

* * * * *

UNITED STATES PATENT AND TRADEMARK OFFICE
CERTIFICATE OF CORRECTION

| | | |
|---|---|---|
| PATENT NO. | : 9,220,263 B2 | Page 1 of 1 |
| APPLICATION NO. | : 12/742153 | |
| DATED | : December 29, 2015 | |
| INVENTOR(S) | : Petra Claire Farquhar Oyston and Graeme Christopher Clark | |

It is certified that error appears in the above-identified patent and that said Letters Patent is hereby corrected as shown below:

On the Title Page:

Item (73) "The Secretary of State for Defense" should be corrected to read -- The Secretary of State for Defence --

Signed and Sealed this
Twenty-sixth Day of April, 2016

Michelle K. Lee
*Director of the United States Patent and Trademark Office*

SEQUENCE LISTING

```
<160> NUMBER OF SEQ ID NOS: 7

<210> SEQ ID NO 1
<211> LENGTH: 1764
<212> TYPE: DNA
<213> ORGANISM: Yersinia pestis

<400> SEQUENCE: 1
atgcttcaaa tagataatgt cattaataat attggaaact actttcatca tctaagtaac      60
attaattata tacgacttct ggatacccccc catgcttggg gagccccatt tggtaaagaa     120
atcatgcagc aatcttactt acggcaagag gagtttgcag gggcaatgac tgaagtactg     180
cggaattcgc gttatcgctg tgatatatca tcacttaata gccccgatgc agagtggcga     240
aaagtgattt ttaaggccat tgatgaatcc ttatcgaaaa aaatggggcg aactcagcca     300
actcagtata ggtttctttt cggccaatct ccaacagtat ttatgaatgg gttatctgct     360
gcaacaaatg gctcccctga ctttgttgct tttaaatcag agttaattca gctaattaag     420
gagcgaggac aatattggga aaaaatgcct gaaatttggc taggccgttt ctttagaata     480
gaagaagggt tggctacatc atttatgaga aacgtgtatc ctgatttccc accaatcaac      540
gatacaagaa tgcatggaa tcacacaaaa ataatggcct cagatggtac tgaagctctt     600
gttggtggac ataacatgaa catggatcta tttagaaatt atccacctgt tcatgatgta     660
tcaattatca ctcatggttc ttctgcttat ggctcccagc tatatcttaa cgaactatgg     720
tcatgtaatt cagatttact aaaaaaagaa tattttgatt atgaaagcat gatgtgggcg     780
gtcggaacaa agttctatga taagcctgaa gatccgctta aaagctcagt tgctatgaat     840
tatatgaagc aacggcaaga ggacctactc aacttgcatg aaaactttaa tcagaaggta     900
gcgactcgta ttagtgaata cgaaaacatg gaagagtata aaaaagcaga cagagtttta     960
tcagtaggta aatattggac aggacctaat atggagcatg actaccaaag agggtctgaa    1020
ataatgaaag agcaactgat aaaaaatgct aagcgcataa ttagaatttc acagcaagat    1080
ctcgtgagtg cttggaaaaa aaatggaaa gaccacttta cgtgtaattg gattattgag    1140
gctttgttag aaaataaaga tcttcatatt catgttgtag tctctgctct agatgcagca    1200
gctggagctg ctggtgatca gtactcattt ggttctggag cagaacggac ctatgaatta    1260
tttaagtatt acctaaccca tgatattgat accgatgaag tattagacga tcctgatggt    1320
agccgtgctg atgccttaaa aagaatattg attgcaccat tcttctttac agataaagta    1380
cctgatgaaa atacaattga aggcgaaacc tacaagtggc ctgatttaga acaaagcgct    1440
tatactgcaa cacttaagca aaaccacctt tcggaaaaac ccccgcatca aggtattatt    1500
ggtagtgcac taatgtcagc aattaaaggt agtggacttt tctatcctaa agtccctgtt    1560
```

```
gcacctggta atcacgccaa attaatgatt attgacgatg agttgtacgt tgttggatca   1620
gataatcttt atcccggtta tctgtcagag tttgactatt tagtcgaagg aaaagatgca   1680
gttaatgaat taatgaaatc ttactgggaa ccattgtgga aatattctag cccacatgca   1740
tttccaaaat taagcccaaa ttaa                                          1764
```

<210> SEQ ID NO 2
<211> LENGTH: 587
<212> TYPE: PRT
<213> ORGANISM: Yersinia pestis

<400> SEQUENCE: 2

```
Met Leu Gln Ile Asp Asn Val Ile Asn Asn Ile Gly Asn Tyr Phe His
1               5                   10                  15

His Leu Ser Asn Ile Asn Tyr Ile Arg Leu Leu Asp Thr Pro His Ala
            20                  25                  30

Trp Gly Ala Pro Phe Gly Lys Glu Ile Met Gln Gln Ser Tyr Leu Arg
        35                  40                  45

Gln Glu Glu Phe Ala Gly Ala Met Thr Glu Val Leu Arg Asn Ser Arg
    50                  55                  60

Tyr Arg Cys Asp Ile Ser Ser Leu Asn Ser Pro Asp Ala Glu Trp Arg
65                  70                  75                  80

Lys Val Ile Phe Lys Ala Ile Asp Glu Ser Leu Ser Lys Lys Met Gly
                85                  90                  95

Arg Thr Gln Pro Thr Gln Tyr Arg Phe Leu Phe Gly Gln Ser Pro Thr
            100                 105                 110

Val Phe Met Asn Gly Leu Ser Ala Ala Thr Asn Gly Ser Pro Asp Phe
        115                 120                 125

Val Ala Phe Lys Ser Glu Leu Ile Gln Leu Ile Lys Glu Arg Gly Gln
    130                 135                 140

Tyr Trp Glu Lys Met Pro Glu Ile Trp Leu Gly Arg Phe Phe Arg Ile
145                 150                 155                 160

Glu Glu Gly Leu Ala Thr Ser Phe Met Arg Asn Val Tyr Pro Asp Phe
                165                 170                 175

Pro Pro Ile Asn Asp Thr Arg Met Thr Trp Asn His Thr Lys Ile Met
            180                 185                 190

Ala Ser Asp Gly Thr Glu Ala Leu Val Gly Gly His Asn Met Asn Met
        195                 200                 205

Asp Leu Phe Arg Asn Tyr Pro Pro Val His Asp Val Ser Ile Ile Thr
    210                 215                 220

His Gly Ser Ser Ala Tyr Gly Ser Gln Leu Tyr Leu Asn Glu Leu Trp
225                 230                 235                 240

Ser Cys Asn Ser Asp Leu Leu Lys Lys Glu Tyr Phe Asp Tyr Glu Ser
                245                 250                 255

Met Met Trp Ala Val Gly Thr Lys Phe Tyr Asp Lys Pro Glu Asp Pro
            260                 265                 270

Leu Lys Ser Ser Val Ala Met Asn Tyr Met Lys Gln Arg Gln Glu Asp
        275                 280                 285

Leu Leu Asn Leu His Glu Asn Phe Asn Gln Lys Val Ala Thr Arg Ile
    290                 295                 300

Ser Glu Tyr Glu Asn Met Glu Glu Tyr Lys Lys Ala Asp Arg Val Leu
305                 310                 315                 320

Ser Val Gly Lys Tyr Trp Thr Gly Pro Asn Met Glu His Asp Tyr Gln
                325                 330                 335
```

Arg Gly Ser Glu Ile Met Lys Glu Gln Leu Ile Lys Asn Ala Lys Arg
                340                 345                 350

Ile Ile Arg Ile Ser Gln Gln Asp Leu Val Ser Ala Trp Lys Lys Lys
            355                 360                 365

Trp Lys Asp His Phe Thr Cys Asn Trp Ile Ile Glu Ala Leu Leu Glu
370                 375                 380

Asn Lys Asp Leu His Ile His Val Val Ser Ala Leu Asp Ala Ala
385                 390                 395                 400

Ala Gly Ala Ala Gly Asp Gln Tyr Ser Phe Gly Ser Gly Ala Glu Arg
                405                 410                 415

Thr Tyr Glu Leu Phe Lys Tyr Tyr Leu Thr His Asp Ile Asp Thr Asp
            420                 425                 430

Glu Val Leu Asp Asp Pro Asp Gly Ser Arg Ala Asp Ala Leu Lys Arg
                435                 440                 445

Ile Leu Ile Ala Pro Phe Phe Phe Thr Asp Lys Val Pro Asp Glu Asn
450                 455                 460

Thr Ile Glu Gly Glu Thr Tyr Lys Trp Pro Asp Leu Glu Gln Ser Ala
465                 470                 475                 480

Tyr Thr Ala Thr Leu Lys Gln Lys Pro Leu Ser Glu Lys Pro Pro His
                485                 490                 495

Gln Gly Ile Ile Gly Ser Ala Leu Met Ser Ala Ile Lys Gly Ser Gly
            500                 505                 510

Leu Phe Tyr Pro Lys Val Pro Val Ala Pro Gly Asn His Ala Lys Leu
            515                 520                 525

Met Ile Ile Asp Asp Glu Leu Tyr Val Val Gly Ser Asp Asn Leu Tyr
            530                 535                 540

Pro Gly Tyr Leu Ser Glu Phe Asp Tyr Leu Val Glu Gly Lys Asp Ala
545                 550                 555                 560

Val Asn Glu Leu Met Lys Ser Tyr Trp Glu Pro Leu Trp Lys Tyr Ser
                565                 570                 575

Ser Pro His Ala Phe Pro Lys Leu Ser Pro Asn
                580                 585

<210> SEQ ID NO 3
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 3
cgggatccta atgcttcaaa tagataa                                27

<210> SEQ ID NO 4
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 4
gtcctcgagt taatttgggc ttaattttgg                             30

<210> SEQ ID NO 5
<211> LENGTH: 31
<212> TYPE: DNA
<213> ORGANISM: Artificial sequence
<220> FEATURE:

-continued

```
<223> OTHER INFORMATION: Synthetic sequence: Primer

<400> SEQUENCE: 5
gtcatgcata tgcttcaaat agataatctc a                              31

<210> SEQ ID NO 6
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 6
gtcggatcct taatttgggc ttaattttgg                                30

<210> SEQ ID NO 7
<211> LENGTH: 50
<212> TYPE: DNA
<213> ORGANISM: Artificial sequence
<220> FEATURE:
<223> OTHER INFORMATION: Synthetic sequence: Primer

<400> SEQUENCE: 7
gacgtcgact tagtgatggt gatggtgatg atttgggctt aattttggaa          50
```